US010260168B2

(12) United States Patent
Lee et al.

(10) Patent No.: US 10,260,168 B2
(45) Date of Patent: Apr. 16, 2019

(54) MICROFLUIDIC DEVICES AND METHODS

(75) Inventors: Abraham Lee, Irvine, CA (US); Philip Felgner, Rancho Santa Fe, CA (US); Armando Tovar, Newport Beach, CA (US); Uland Liao, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 733 days.

(21) Appl. No.: 13/400,255

(22) Filed: Feb. 20, 2012

(65) Prior Publication Data
US 2012/0149600 A1  Jun. 14, 2012

Related U.S. Application Data

(60) Division of application No. 12/123,389, filed on May 19, 2008, now abandoned, which is a
(Continued)

(51) Int. Cl.
*C40B 60/12* (2006.01)
*B01L 3/00* (2006.01)
(Continued)

(52) U.S. Cl.
CPC ........ *C40B 60/12* (2013.01); *B01L 3/502715* (2013.01); *G01N 21/05* (2013.01); *G01N 21/78* (2013.01); *G01N 21/82* (2013.01); *G01N 33/54366* (2013.01); *G01N 33/581* (2013.01); *G01N 33/6803* (2013.01); *G01N 33/6845* (2013.01); *B01J 2219/0061* (2013.01); *B01J 2219/00315* (2013.01);
(Continued)

(58) Field of Classification Search
CPC ........ C40B 60/12; G01N 21/05; G01N 21/78; G01N 21/82; G01N 33/54366; G01N 33/581; G01N 33/6845; G01N 33/6803; B01L 3/502715; Y02A 50/58; Y02A 50/394; Y02A 50/412
See application file for complete search history.

(56) References Cited

U.S. PATENT DOCUMENTS

| 5,516,638 A | 5/1996 | Urnotitz et al. |
| 5,836,683 A | 11/1998 | Moon et al. |

(Continued)

FOREIGN PATENT DOCUMENTS

| WO | 00/62073 | 10/2000 |
| WO | 2005/118885 | 12/2005 |
| WO | 2006/088492 | 8/2006 |

OTHER PUBLICATIONS

Liu et al. Bubble-induced acoustic micromixing, Lab on a chip, 2002, vol. 2, pp. 151-157.*
(Continued)

*Primary Examiner* — Melanie Brown
(74) *Attorney, Agent, or Firm* — Fish IP Law, LLP

(57) ABSTRACT

Contemplated microfluidic devices and methods are drawn to protein arrays in which distinct and detergent-containing antigen preparations are deposited onto an optical contrast layer in a non-specific and non-covalent manner. Detection of binding a is carried out using a dye that precipitates or agglomerates to so form a visually detectable signal at a dynamic range of at least three orders of magnitude.

11 Claims, 5 Drawing Sheets

Related U.S. Application Data continuation-in-part of application No. PCT/US2005/023352, filed on Jul. 1, 2005.

(60) Provisional application No. 60/938,983, filed on May 18, 2007, provisional application No. 60/638,624, filed on Dec. 23, 2004, provisional application No. 60/585,351, filed on Jul. 1, 2004.

(51) Int. Cl.

| | |
|---|---|
| G01N 21/05 | (2006.01) |
| G01N 21/78 | (2006.01) |
| G01N 21/82 | (2006.01) |
| G01N 33/543 | (2006.01) |
| G01N 33/58 | (2006.01) |
| G01N 33/68 | (2006.01) |
| G01N 21/77 | (2006.01) |
| G01N 21/03 | (2006.01) |

(52) U.S. Cl.
CPC .............. *B01J 2219/00479* (2013.01); *B01J 2219/00531* (2013.01); *B01J 2219/00608* (2013.01); *B01J 2219/00612* (2013.01); *B01J 2219/00617* (2013.01); *B01J 2219/00621* (2013.01); *B01J 2219/00626* (2013.01); *B01J 2219/00635* (2013.01); *B01J 2219/00637* (2013.01); *B01L 2300/0654* (2013.01); *G01N 2021/0346* (2013.01); *G01N 2021/054* (2013.01); *G01N 2021/058* (2013.01); *G01N 2021/7763* (2013.01); *G01N 2021/7773* (2013.01); *G01N 2021/825* (2013.01); *Y02A 50/394* (2018.01); *Y02A 50/412* (2018.01); *Y02A 50/58* (2018.01)

(56) References Cited

U.S. PATENT DOCUMENTS

| | | | | |
|---|---|---|---|---|
| 6,214,560 | B1* | 4/2001 | Yguerabide | C12Q 1/6816 422/50 |
| 6,344,337 | B1 | 2/2002 | Mansfield et al. | |
| 6,515,039 | B1* | 2/2003 | Ulbricht | B01J 19/0046 506/3 |
| 6,844,163 | B1 | 1/2005 | Matsuzawa et al. | |
| 6,887,701 | B2 | 5/2005 | Anderson et al. | |
| 8,449,171 | B2* | 5/2013 | Tho et al. | 366/108 |
| 8,591,093 | B2* | 11/2013 | Schoenfeld | 366/108 |
| 2002/0055186 | A1* | 5/2002 | Barry | C40B 30/04 436/518 |
| 2002/0101646 | A1* | 8/2002 | Ide | G01B 7/287 359/295 |
| 2002/0171037 | A1* | 11/2002 | Ellson et al. | 250/288 |
| 2003/0044317 | A1* | 3/2003 | Catt et al. | 422/58 |
| 2003/0108949 | A1 | 6/2003 | Bao et al. | |
| 2003/0175947 | A1* | 9/2003 | Liu et al. | 435/288.5 |
| 2003/0228637 | A1* | 12/2003 | Wang | 435/7.9 |
| 2004/0072231 | A1* | 4/2004 | Mirkin | B82Y 15/00 435/6.12 |
| 2004/0161748 | A1 | 8/2004 | He et al. | |
| 2004/0183964 | A1* | 9/2004 | Misewich | G02F 1/0551 349/113 |
| 2005/0031488 | A1 | 2/2005 | Ge et al. | |
| 2005/0048580 | A1 | 3/2005 | Labaer et al. | |
| 2005/0074784 | A1 | 4/2005 | Vo-Dinh | |
| 2005/0142664 | A1 | 6/2005 | Loney | |
| 2006/0019265 | A1* | 1/2006 | Song et al. | 435/6 |
| 2006/0224329 | A1 | 10/2006 | Roth et al. | |
| 2007/0020678 | A1 | 1/2007 | Ault-Riche et al. | |

OTHER PUBLICATIONS

D. G. Schiavini, et al. "Quantitative Western Immunoblotting Analysis in Survey of Human Immunodeficiency Virus-Seropositive Patients". Journal of Clinical Microbiology, Sep. 1989, p. 2062-2066.

Schultz-Geshcwender, A. et. al. "Quantitative, Two-Color Western Blot Detection With Infrared Fluorescence". LI-COR Biosciences, Lincoln, Nebraska 68504.

Ornberg, R. L et al. "Western blot analysis with quantum dot fluorescence technology: a sensitive and quantitative method for multiplexed proteomics". Nature Methods, 2: 79-81.

Mathrubutham, M. et al. "Methods and considerations for quantitative Western blotting using SuperSignal® Chemiluminescent Substrates". Pierce Application Notes, AN0012.0.

Feissner, R. et al. "Chemiluminescent-based methods to detect subpicomole levels of c-type cytochromes." Anal Biochem. Apr. 1, 2003;315(1):90-4. Department of Biology, Washington University, St. Louis, MO 63130, USA.

* cited by examiner

MICROFLUIDIC DEVICES AND METHODS

This application is a divisional application of co-pending U.S. application with the Ser. No. 12/123,389, which was filed May 19, 2008, which is a continuation-in-part of International patent application with the serial number PCT/US05/23352 (published as WO 06/088492, incorporated by reference herein), which was filed Jul. 1, 2005, and which claims priority to U.S. provisional applications with the Ser. Nos. 60/585,351 and 60/638,624, which were filed Jul. 1, 2004, and Dec. 23, 2004, respectively. This application further claims priority to copending U.S. provisional application with the Ser. No. 60/938,983, which was filed May 18, 2007, and which is incorporated by reference herein.

FIELD OF THE INVENTION

The field of the invention is diagnostic devices and methods, especially as it relates to microfluidic protein microarray devices.

BACKGROUND

Automated diagnostic devices based on molecular biological technology are vital for rapidly confirming presence and identity of pathogens. In many cases, detection of the pathogens employs polymerase-chain-reaction (PCR) as such reaction affords very high sensitivity. On the other hand, and especially in the point-of care market, antibody-based methods enjoy relatively high popularity due to their simple use and disposability. However, most antibody-based tests fail to provide a multiplex format, especially where the test is in the point-of care market.

Recently, various microarray tests and test formats have been developed to allow analysis of several ten to several ten thousand analytes in a biological sample. However, as the analyte spot size on the array has become increasingly smaller, optical detection has become more and more complex. Most typically, currently known microarray tests require conventional lab-bench methods that often require whole-day processes and large amounts of user-handling confined to laboratory settings. Moreover, where the array is relatively small, dedicated detection devices (e.g., to detect fluorescence, luminescence, etc.) operate in conjunction with confocal or other magnifying optics, rendering such devices less suitable for field use.

For example, U.S. patent application 2005/031488 teaches an array of isolated proteins immobilized onto a membrane in a dot blot format where the membrane is suspended in a frame for simplified handling. While such array is relatively simple to handle, quantitative analysis is typically not possible and where large numbers of peptides are required, the size of such arrays is prohibitive to high-throughput screening. Still further, such arrays require isolated and purified protein, which adds substantial effort to the construction of the array. To increase density of the array, multiple fibers coated with selected and purified antigens can be bundled and sliced to produce an array as taught in U.S. Pat. No. 6,887,701. Detection in these arrays can use various formats, and is typically done via fluorescence detection. Such array significantly increases the analyte density, however, is typically limited to qualitative detection of reagents. Moreover, the preparation of such arrays is labor intensive and typically requires isolated compounds.

To circumvent problems associated with isolated peptides, individual clones of a nucleic acid library can be expressed in vitro as taught in U.S. application 2004/161748 or in situ as taught in U.S. application 2005/048580. Similarly, epitope arrays can be expressed in vitro as taught in U.S. application 2006/224329. The recombinant protein is then immobilized to the array carrier using a tag or affinity peptide that is fused to the recombinant protein. While such methods significantly simplify array production and increase probe density, various difficulties nevertheless remain. For example, the recombinant protein preparations must be purified and so add substantial effort. Moreover, quantitative detection is typically limited to fluorescence and/or luminescence methods, which require dedicated and expensive devices.

Compounding difficulties with current antibody-test methods is the fact that most or all methods require highly purified protein to be deposited on to a carrier, especially where quantitative analysis of signals is required. Where such carrier is transparent, attachment of unpurified or partially purified proteins typically fail. Alternatively, nitrocellulose membranes may be employed to couple unpurified or partially purified proteins to the carrier. However, under all or almost all circumstances, quantitative analysis of nitrocellulose bound antigens using antibody methods is not possible. Where such quantitative detection was attempted, detection was limited to fluorometric or chmiluminometric detection (see e.g., Schiavini, D. G., et al. (1989). Quantitative Western immunoblotting analysis in survey of human immunodeficiency virus-seropositive patients. J. Clin. Microbiol. 27: 2062-2066; or Feissner, R., et al. (2003). Chemiluminescent-based methods to detect subpicomole levels of c-type cytochromes. Anal. Biochem. 315: 90-94).

Therefore, while numerous methods of microarray tests are known in the art, all or almost all of them suffer from one or more disadvantages. Consequently, there is still a need to provide improved devices and methods to simplify and improve quantitative analysis in antibody-based microarray devices.

SUMMARY OF THE INVENTION

The present invention provides significantly improved apparatus, systems and methods in which antibody-based protein array analysis allows for quantitative detection of antigens and/or antibodies from crude protein preparations using a precipitating or agglomerating dye that is visually detectable. Particularly preferred systems are configured as microfluidic systems and provide a dynamic range of at least three orders of magnitude, while analysis can be completed in less than one hour.

In one especially preferred aspect of the inventive subject matter, a method of performing an analytic test will include a step of providing a carrier having a surface that comprises an optical contrast layer, wherein a plurality of detergent-containing non-purified distinct antigen preparations are non-covalently and non-specifically coupled to the optical contrast layer at respective predetermined locations to form an antigen array having a density of at least 10 distinct antigen preparations per $cm^2$. Most preferably, the optical contrast layer has a thickness and composition sufficient to prevent confluence of the antigen preparations when the distinct antigen preparations are deposited onto the optical contrast layer. In a further step, the antigen array is contacted with a solution comprising an antibody (typically human blood or serum) under conditions to allow binding of the antibody to an antigen of at least one of the antigen preparations. In a still further step, binding of the antibody is detected using a visually detectable, and precipitating or agglomerating dye.

In especially preferred methods, the contrast layer and the antigen preparations have a composition such that the step of detecting binding of the antibody allows detection over a dynamic range of at least three orders of magnitude, and/or the array comprises at least two distinct antigens from the same pathogen, most preferably with known quantified and known relative reactivities with respect to sera of a population infected with the pathogen.

With respect to suitable dyes in contemplated methods it is once more preferred that the dye is insoluble in the developing medium to precipitate in situ. For example, contemplated dyes therefore include 3-amino-9-ethylcarbazole, 5-bromo-4-chloro-3-indolylphosphate, 3-3'-diaminobenzidine tetrachloride, 3,3',5,5'-tetramethylbenzidine. Alternatively, colloidal gold or other colloidal metals may be employed as a dye. Consequently, it should be appreciated that detection can be performed with the unaided eye using no further detection devices such as luminometers or fluorimeters. However, where quantification is desired, it is preferred that the step of detecting is performed using a scanner or CCD detector. Remarkably, using an ordinary commercially available flat bed scanner with a resolution of 1200 dpi, quantitative analysis at a dynamic range of at least three orders of magnitude can be achieved. Moreover, where desired, the step of detecting is performed from opposite sides of the optical contrast layer.

Therefore, in another aspect of the inventive subject matter, contemplated microfluidic devices will comprise an enclosed reaction volume formed by a carrier material such that an optical contrast layer is disposed within the reaction volume and opposite to a cavity layer within the reaction volume, wherein a plurality of distinct antigens are non-covalently and non-specifically coupled to the optical contrast layer in predetermined positions. Additionally, it is preferred that the distinct antigens are non-purified and further comprise a detergent. Most typically, the cavity layer has plurality of cavities (preferably opposite the contrast layer) that are sized and dimensioned to allow trapping of air in the plurality of cavities, wherein the number and/or size of the cavities is selected such that hybridization of an antibody to the antigens is substantially complete within less than 60 minutes upon mixing. It is still further preferred that is such devices the carrier material is configured to allow quantitative detection of a visually detectable, and precipitating or agglomerating dye.

In especially preferred devices, the optical contrast layer comprises nitrocellulose, and/or the carrier material comprises a glass and/or transparent synthetic polymer. It is further preferred that the cavities in the cavity layer in contemplated microfluidic devices are circular cavities and perpendicularly arranged at regular intervals along an x- and y-coordinate. In such devices, the ratio between the number of antigens and the number of cavities is at least 3:1, and/or the ratio between the area of an antigen spot and the cavity diameter is at least 1:3. Typically, the reaction volume is between 1 μl and 500 μl, and most typically between 1 μl and 50 μl.

In yet further aspects of contemplated microfluidic devices, the carrier material and the optical contrast layer are configured to allow quantitative detection over a dynamic range of at least three orders of magnitude, and quantitative detection is based on a dye that is insoluble in the detection solution (e.g., 3-amino-9-ethylcarbazole, 5-bromo-4-chloro-3-indolylphosphate, 3-3'-diaminobenzidine tetrachloride, 3,3',5,5'-tetramethylbenzidine, and a colloidal metal) to so form a visually detectable spot. Where desirable, the carrier material and/or the optical contrast layer are configured to allow optical detection from opposite sides of the optical contrast layer.

Various objects, features, aspects and advantages of the inventive subject matter will become more apparent from the following detailed description of preferred embodiments, along with the accompanying drawings in which like numerals represent like components.

DETAILED DESCRIPTION

Figure 1:
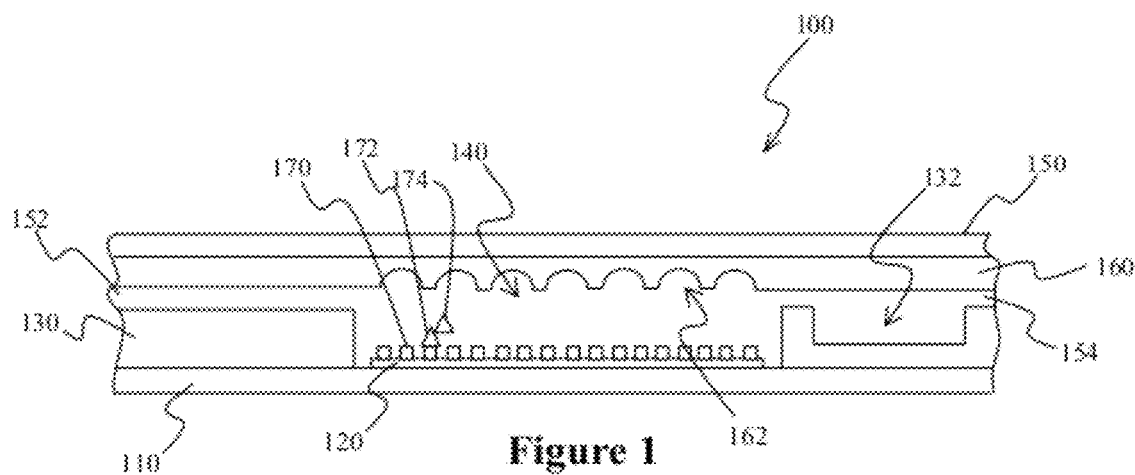
FIG. 1 schematically depicts an exemplary microfluidic device.

The inventors have now discovered that protein microarrays can be miniaturized to high densities, even when unpurified or partially purified proteins are used, and that such microarrays can be processed in various microfluidic devices at a heretofore not achieved speed while at the same time allowing for simple colorimetric signal generation and detection at a remarkably high dynamic range.

In one preferred aspect, proteins corresponding to selected antigens of known pathogens are separately arrayed and non-covalently immobilized onto a nitrocellulose substrate that also acts as an optical contrast layer wherein the nitrocellulose is most preferably coupled to a glass carrier or other carrier that is optically transparent. The so immobilized antigens are then used to specifically capture antibodies present within a serum sample. Among various other unexpected advantages, it should be particularly pointed out that the antigens for such arrays need not be purified at all (or may only be partially purified), and suitable antigen sources therefore include crude in vitro translation reactions (which may also be used in situ where desired). Thus, the term "unpurified antigen" as used herein refers to an antigen that is present together the contents of a bacterial (*E. coli*), yeast (e.g., *Pichia pasteuris*), or eukaryotic cell (e.g., Sf9 or CHO cells), or components hereof suitable for in vitro translation. Viewed from another perspective, unpurified antigens will typically be applied to the optical contrast layer as an aliquot of an in vitro or in situ translation/expression reaction. Similarly, the term "partially purified antigen" as used herein refers to an antigen preparation (typically the unpurified antigen as defined above) after the preparation was subjected to a step of filtration, fractionated precipitation, solvent extraction, and/or centrifugation. However, electrophoretically separated antigens and affinity purified antigens are expressly excluded from the definition of the terms "unpurified antigen" and "partially purified antigen". There are numerous methods of preparing such contemplated antigens known in the art, and all of the known methods are deemed suitable for use herein. For example, methods described in WO 02/097051 and WO 2006/088492 (both of which are incorporated by reference herein) may be used to produce relatively large libraries of antigens.

On the other hand, where relatively few antigens are needed, or where selected antigens are already available in purified form, it should be appreciated that the antigens may be applied to the optical contrast layer in substantially purified form (i.e., at least 60%, and more typically at least 75% electrophoretic purity as evidenced by using bromophenol blue staining). Purification may be performed in numerous manners, and especially preferred manners include affinity and ion exchange chromatography. Therefore, suitable antigens may be recombinant and expressed as a fusion protein with affinity tag, or native and directly isolated from the pathogen. In still further contemplated methods and devices, the antigen may also comprise an isolated antigenic epitope of a known larger antigen, and even fusion constructs of multiple antigenic epitopes.

In still further contemplated aspects of the inventive subject matter, it is preferred that the antigen is combined with one or more detergents before the antigen is deposited onto the optical contrast layer. While not wishing to be bound by any theory or hypothesis, it is contemplated that the detergent renders the antigen more available to both non-specific and non-covalent binding to the optical contrast layer, and also more available within the other components of the unpurified antigen for antibody binding. Still further, presence of the detergent is further thought to also render membrane bound and otherwise hydrophobic epitopes available for antibody binding. In especially preferred aspects, the detergent is selected from the group of a polysorbate surfactant (e.g., Tween 80), an alkylglycoside (e.g., octylglycoside), an alkylsulfate (e.g., SDS), and various quaternary ammonium detergents (e.g., cetyl trimethylammonium bromide). Most typically, and depending on the particular detergent used, the detergent will be present at a concentration of between about 0.01 wt % to about 1 wt %, and even more typically between about 0.05 wt % to about 0.1 wt %. The antigen preparation is then applied onto the optical contrast layer using conventional methods such as pin spotting, or nano/picoliter syringe deposition. Typical amounts of antigen deposited per spot will be between about 1 microliter and 1 picoliter, more typically between 100 nanoliter and 10 picoliter, and most typically between 50 nanoliter and 100 picoliter.

With respect to the optical contrast layer it is especially preferred that the layer provides an at least opaque surface (and even more preferably a non-transparent, white, or off-white surface) and that the contemplated that optical contrast layer also allows for non-specific and typically non-covalent coupling of the antigen to the optical contrast layer. Therefore, especially contemplated optical contrast layers will comprise nitrocellulose, polyvinylidenedifluoride (PVDF), or polyethersulfone (PES), preferably at a thickness between 10 and 100 microns, and most preferably at a thickness of between 10 and 20 microns (which allows deposition of antigen spots without confluence). Preferred pore size of such membranes is typically between 0.2 micron and 0.5 micron. Where it is desired that the contrast is relatively high, the carrier may be rendered non-transparent using etching, staining, or sanding (where the carrier is glass or a transparent polymer). Alternatively, non-transparent layers are also deemed suitable for use herein. In still further contemplated aspects, the carrier and the optical contrast layers may form an integrated structure. However, it is generally preferred that the carrier is a glass or polymer (optionally stained) slide and that the optical contrast layer is coupled to the slide using conventional methods.

Suitable array sizes will typically vary from test to test, however, it is generally preferred that the array is on a nitrocellulose (or other protein-binding) membrane having an area of less than 1 $cm^2$, more typically less than 100 $mm^2$, even more typically less than 50 $mm^2$, and most typically less than 40 $mm^2$. Protein spot size will typically vary also, however, it is generally preferred that the spot size is between 10 μm and 1000 μm, more preferably between 50 μm and 500 μm, and most preferably between 100 μm and 300 μm (diameter or largest dimension). Therefore, contemplated arrays will have a density of protein spots between 1-1000 spots/$cm^2$, more typically between 10-500 spots/$cm^2$, and most typically between 100-300 spots/$cm^2$.

In one typical exemplary configuration, a nitrocellulose membrane (12 micron thickness, 0.45 micron pore size) is configured as a square pad of approximately 6 mm by 6 mm in area, and is coupled to a glass slide. Antigens (typically unpurified antigens) are then pin-spotted to the nitrocellulose membrane acting as optical contrast layer to form an array of antigen spots with each spot at approximately 100 to 200 micrometers in diameter. The nitrocellulose layer is then coupled to a glass slide to form the bottom of a chamber, which is then covered by side walls and a top cavity layer (infra). The chamber in such configurations will typically have a volume of between 3-4 microliter and is typically formed from the side walls and top cavity layer using standard soft lithography methods. Therefore, in especially preferred configurations, the antigen array is disposed within a closed chamber that is accessible only via fluid or reagent inflow port(s) and fluid or reagent outflow port(s). It should be noted that conventional Western blot lab-bench methods require pipettes to introduce reagent volumes atop an open-air chamber placed over the array. Reagent volumes in known methods are then removed via aspiration, thus allowing for ambient air contamination and reagent evaporation, which is typically resolved by incubating within a 4° C. environment.

More significantly, it should be appreciated that due to the relatively large volumes in currently known devices, the antibody-antigen binding interactions are solely diffusion-based and therefore require long incubation times. In contrast, the microfluidic approach contemplated herein uses a micro-scale platform enclosed within a low volume reaction chamber (e.g., made from poly-dimethylsiloxane (PDMS) and a glass slide) that reduces exposure and contamination to the outside environment as well as reagent evaporation. Reagent introduction is controllable and can be manipulated using a micro-syringe pump or other known microfluidics methods. It should still further be especially appreciated that antigen-antibody hybridization is additionally favored in preferred configurations by not only selecting a small chamber volume, but also by employing an active mixing configuration. Here, the inventors discovered that hybridization and wash times can be significantly reduced when certain parameters (e.g., ratio between mixing plate cavities, cavity volume and size, and array area) are observed. In such devices, active acoustic resonance 'on-chip' micromixing can be used enhance antibody-antigen binding collisions to overcome limitations associated with slow diffusion-based interactions. With respect to the volume of contemplated chambers in which the nitrocellulose membrane is disposed, it is generally preferred that the volume is between 0.1 µl and 100 µl, more preferably between 1 µl and 50 µl, and most preferably between 2 µl and 20 µl. Suitable chambers will have at least one, and more typically two fluid ports for entry and exit of reagents and samples, and fluid entry may be parallel or perpendicular to the nitrocellulose membrane.

In especially preferred aspects of the inventive subject matter, the chamber has a roof portion (typically opposite to the array) that is configured as a cavity layer to include a plurality of (most preferably circular) cavities with 100 micrometers in diameter and 25 micrometers in height, wherein the cavities are arrayed along the top surface of the inner chamber. The cavities form air pockets during reagent introduction (to so permit bubble formation) that can act as a micromixer when acoustically resonated. The chamber is closed by a cover that is preferably bonded to the structure over the pad using plasma oxidation surface treatment. It should further be appreciated that several factors significantly affect acoustic bubble-array configurations, and especially resonating and mixing capabilities of such configurations. Among other factors, cavity size and depth have proven to be of importance, however, performance was most significantly affected by the bubble cavity distance (this distance is described as the edge to edge spacing between each subsequent bubble cavity within an array as described in more detail below).

Figure 2:
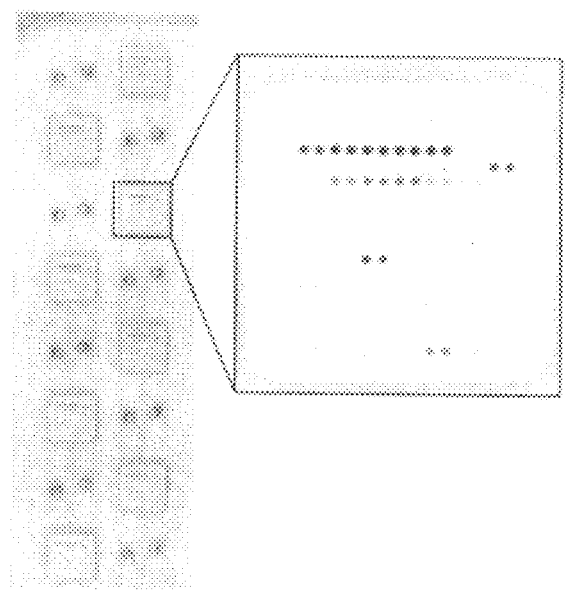
FIG. 2 is an exemplary detail view of glass carrier onto which multiple and distinct nitrocellulose layers are coupled and where multiple and distinct protein antigens are arrayed on the nitrocellulose layers.

An exemplary device is schematically depicted in FIG. 1 in which microfluidic device 100 has a transparent glass carrier 110 to which opaque optical contrast layer 120 is coupled. Intermediate layer 130 (preferably transparent) is shaped to form the sidewalls of chamber 140 that defines the reaction volume. Chamber 140 receives fluids from inlet port 152 (or internal reservoir, not shown) and delivers fluid from the chamber to an internal reservoir 132 that may be formed within the intermediate layer 130. Most typically, the chamber 140 is also fluidly coupled to an outlet or venting port 154. A cavity layer 160 is disposed on top of the intermediate layer 130 and has a plurality of cavities 162, wherein the cavity layer also forms the roof of the reaction volume 140. Opposite the cavity layer is the optical contrast layer 120 to which a plurality of distinct and typically unpurified antigens 170 are non-specifically and non-covalently coupled. Bound to at least one of the antigens is serum antibody 172 and secondary detection antibody 174 that comprises an enzyme or other entity suitable for enzymatic conversion of a chromogenic dye to a dye (not shown) that is insoluble in the detection medium to so form a visually detectable colored signal in situ. The topmost layer 150 is preferably a transparent layer that concludes the architecture of the microfluidics device. Of course, it should be appreciated that two or more of the distinct layers shown in the figure may be combined into a single layer. FIG. 2 depicts another exemplary device in which multiple nitrocellulose membranes are disposed on a glass slide and in which multiple protein antigens are arrayed in a horizontal line, and in which each line represents a different pathogen.

Thus, contemplated microfluidic devices will typically comprise an enclosed reaction volume formed by a carrier material such that an optical contrast layer is disposed within the reaction volume and opposite to a cavity layer within the reaction volume, wherein a plurality of distinct (typically non-purified) antigens are non-covalently and non-specifically coupled to the optical contrast layer in predetermined positions. Most typically, the cavity layer has plurality of cavities (preferably opposite the contrast layer) that are sized and dimensioned to allow trapping of air in the plurality of cavities, wherein the number and/or size of the cavities is selected such that hybridization of an antibody to the antigens is substantially complete within less than 120 minutes, more typically within less than 60 minutes, and most typically within less than 45 minutes upon mixing.

It is especially preferred that the cavities in the cavity layer in contemplated microfluidic devices are circular, and perpendicularly arranged at regular intervals along an x- and y-coordinate. In such devices, the ratio between the number of antigens and the number of cavities is at least 2:1, more preferably at least 3:1, and most preferably at least 4:1, and/or the ratio between the area of an antigen spot and the cavity diameter is at least 1:2, more preferably at least 1:3, and most preferably at least 1:4.

In yet further aspects of contemplated microfluidic devices, the carrier material and the optical contrast layer are configured to allow quantitative detection over a dynamic range of at least three orders of magnitude, and quantitative detection is based on a dye that is insoluble in the detection solution to so form a visually detectable spot. Thus, most of the device portion, and particularly the portion that is above and/or below the optical contrast layer will preferably be transparent.

Consequently, in further preferred aspects of the inventive subject matter, detection of a hybridization event of an antibody to an antigen on the nitrocellulose membrane (or other surface of the optical contrast layer) is mediated by formation of a visually detectable dye, which most preferably precipitates or otherwise localizes to the site of dye formation. It is generally preferred that such dye formation is mediated by an enzyme that reacts with a soluble, chromogen to form a colored (or gray) and preferably precipitating dye. There are numerous such systems known in the art (e.g., 3-amino-9-ethylcarbazole, 5-bromo-4-chloro-3-indolylphosphate, 3-3'-diaminobenzidine tetrachloride, 3,3',5, 5'-tetramethylbenzidine, and a colloidal metal), and all of these are deemed suitable for use herein. Alternatively, detection may also involve local concentration of colloidal gold (or other metal) which also leads to formation of a visually detectable dye (can be detected with the unaided eye).

It should be especially appreciated that a person of ordinary skill in the art would not expect that quantitative colorimetric detection in array systems would be achievable, and especially in miniaturized systems (e.g., where the array area is less than 10 mm$^2$). Even more remarkable, the inventors discovered that quantitative colorimetric detection is even possible where the recombinant protein antigen is not purified (e.g., as crude expression reaction) or only partially purified (e.g., present in less than 50% homogeneity). The term "colorimetric" as used herein refers to any dye that has appears colored (or has a grayness) to the unaided eye and that has substantial absorption in the visible wavelength spectrum. Thus, fluorescent or luminescent dyes are excluded from that term.

Therefore, it should be appreciated that contemplated colorimetric detection systems provide several advantages over heretofore alternative, but very limited detection methods (e.g., fluorescence or luminescence). Although well-established in research, fluorometric reaction products require excitation at particular wavelengths and thus necessitate expensive and large-scale equipment that is both fragile and expensive. Similarly, luminometric detection requires highly sensitive detectors and often chemically labile reagents. In contrast, colorimetric detection produces a reaction product that is detectable at visible wavelengths and thus can be analyzed using ordinary optical methods yielding the potential for portability. Most preferably, detection is performed using a CCD detector, which may be in a camera or scanner format. Depending on the degree of miniaturization and antigen density on the array, the detection may include magnifying optics, which may be associated with the CCD detector and/or with the housing. For example, the housing may include a lens that provides magnification for the detector, or the detector is a scanner and the magnification is electronic (e.g., based on 1200 dpi or higher resolution).

Thus, especially preferred methods include those in which a carrier having a surface that comprises an optical contrast layer is provided, wherein a plurality of detergent-containing non-purified distinct antigen preparations are non-covalently and non-specifically coupled to the optical contrast layer at respective predetermined locations to form an antigen array having a density of at least 10 distinct antigen preparations per cm². Most preferably, the optical contrast layer has a thickness and composition sufficient to prevent confluence of the antigen preparations when the distinct antigen preparations are deposited onto the optical contrast layer. The antigen array is then contacted with a solution comprising an antibody (typically human blood or serum) under conditions that allow binding of the antibody to an antigen of at least one of the antigen preparations. Binding of the antibody is detected using a visually detectable, and precipitating or agglomerating dye using secondary antibodies (or fragments thereof) that most typically comprise an enzyme or ligand suitable for a subsequent reaction that forms from a chromogen a precipitating dye.

Such methods advantageously allow concurrent, fast, and simple multiple pathogen detection using nothing more than a minute blood sample and reagents (which may be stored within one or more compartments of the device. Analysis can then be visually performed, and where quantitative analysis is desired, analysis may also include electronic image analysis with or without optical magnification. As discussed above, preferred antigens are typically unpurified or only partially purified. Or diagnostic applications it is particularly preferred that the array comprises at least two distinct antigens from the same pathogen, most preferably with known quantified and known relative reactivities with respect to sera of a population infected with the pathogen. Thus, such diagnostic devices will allow a person not only to ascertain presence or absence of a pathogen, but also to obtain information on the type (chronic, acute, etc.) and/or stage (early, late, treated, etc.) of a disease, and even prognosis of responsiveness to treatment.

EXAMPLES

PCR amplification of linear acceptor vector: Plasmid pXT7 (10 µg; 3.2 kb, KanR) was linearized with BamHI (0.1 µg/µl DNA/0.1 mg/ml BSA/0.2 units/µl BamHI; 37° C. for 4 hr; additional BamHI was added to 0.4 units/µl at 37° C. overnight). The digest was purified using a PCR purification kit (Qiagen, Valencia, Calif.), quantified by fluorometry using Picogreen (Molecular Probes, Carlsbad, Calif.) according to the manufacturer's instructions, and verified by agarose gel electrophoresis (1 µg). One ng of this material was used to generate the linear acceptor vector in a 50-µl PCR using 0.5 µM each of suitable primers, and 0.02 units/µl Taq DNA polymerase (Fisher Scientific, buffer A)/0.1 mg/ml gelatin (Porcine, Bloom 300; Sigma, G-1890)/0.2 mM each dNTP with the following conditions: initial denaturation of 95° C. for 5 min; 30 cycles of 95° C. for 0.5 min, 50° C. for 0.5 min, and 72° C. for 3.5 min; and a final extension of 72° C. for 10 min.

PCR amplification of ORF insert: A total of 1-10 ng of genomic DNA (e.g., *Plasmodium falciparum* 3D7 strain) was used as template in a 50-µl PCR using suitable primers (0.5 µM each). PCR was carried out using regular Taq DNA polymerase: 0.02 units/µl TaqDNA polymerase (buffer A, Fisher Scientific)/0.1 mg/ml gelatin (Bloom 300, Porcine; G-1890, Sigma)/0.2 mM each dNTP. Conditions were as follows: initial denaturation of 95° C. for 5 min; 30 cycles of 20 sec at 95° C., 30 sec at 50° C., and 60 sec/kb at 72° C. (1-3 min on average, based on ORF size); and a final extension of 72° C. for 10 min. PCR products that were more difficult to produce were reamplified by using a 30 sec annealing time at 45° C. or 40° C., instead of 30 sec at 50° C. Also, the extension temperature was decreased from 65-72° C. to 50° C. Subsequently PCR products were obtained using a Taq polymerase with improved proof-reading characteristics (Triplemaster from Eppendorf), increasing the efficiency of the PCR: 0.04 units/µl Triple Master PCR system (high-fidelity buffer, Eppendorf)/0.4 mM each dNTP (Eppendorf). Conditions were as follows: initial denaturation of 95° C. for 3 min; 35 cycles of 15 sec at 95° C., 30 sec at 40° C., and 60 sec/kb at 50° C. (1-3 min on average, based on ORF size); and a final extension of 50° C. for 10 min., PCR products that were difficult were reamplified using 50 ng genomic DNA. The PCR product was visualized by agarose gel electrophoresis (3 µl). For quantification, the product was purified (PCR purification kit, Qiagen) and quantified by fluorometry.

In vivo recombination cloning: Competent cells were prepared by growing DH5α cells at 18° C. in 500 ml of SOB (super optimal broth) medium (2% tryptone/0.5% yeast extract/10 mM NaCl/2.5 mM KCl/20 mM MgSO₄) to an OD of 0.5-0.7. The cells were washed and suspended in 10 ml of pre-chilled PCKMS buffer (10 mM Pipes/15 mM CaCl₂/250 mM KCl/55 mM MnCl₂/5% sucrose, pH 6.7) on ice, and 735 µl of DMSO was added dropwise with constant swirling. The competent cells were frozen on dry ice-ethanol in 100-µl aliquots and stored at −80° C. Each transformation consisted of the following: 10 µA of competent DH5α and 10 µl of DNA mixture (40 ng of PCR-generated linear vector/10 ng of PCR-generated ORF fragment; molar ratio, 1:1; vector, 1-kb ORF fragment). For transformation, the purification of PCR product was unnecessary. The mixture was incubated on ice for 45 min, heat shocked at 42° C. for 1 min, and chilled on ice for 1 min; mixed with 250 µl of SOC (super optimal catabolizer) medium (2% tryptone/0.55% yeast extract/10 mM NaCl/10 mM KCl/10 mM MgCl₂/10 mM MgSO₄/20 mM glucose); incubated at 37° C. for 1 hr; diluted into 3 ml of LB medium supplemented with 50 µg of kanamycin per ml (LB Kan 50); and incubated with shaking overnight. The plasmid was isolated and purified from this culture, without colony selection.

In vitro protein expression: Plasmid templates used for in vitro transcription/translation were prepared by using QIAprep Spin Miniprep kits (Qiagen), including the "optional" step, which contains protein denaturants to deplete RNase activity. In vitro transcription/translation reactions (RTS 100 *Escherichia coli* HY kits; Roche) were set up in 25 µl PCR 12-well strip tubes and incubated for 5 h at 30° C., according to the manufacturer's instructions.

Immuno-dot blots: To assess relative efficiency of protein expression, 0.3 µl of whole rapid-translation system (RTS) reactions were spotted manually onto nitrocellulose and allowed to air dry before blocking in 5% nonfat milk powder in TBS containing 0.05% Tween 20. Blots were probed with hyperimmune sera diluted to 1:1,000 in blocking buffer with or without 10% *E. coli* lysate. Routinely, dot blots were stained with both mouse anti-poly-HIS mAb (clone, HIS-1; H-1029, Sigma) and rat anti-hemagglutinin (HA) mAb (clone, 3F10; 1 867 423, Roche), followed by alkaline phosphatase-conjugated goat anti-mouse IgG (H+L) (Bio-Rad) or goat anti-rat IgG (H+L) (Jackson ImmunoResearch) secondary Abs, respectively. Bound human Abs were visualized with nitroblue tetrazolium (nitro-BT) developer to confirm the presence of protein.

Microarray chip printing: For microarrays, 10 µl of 0.125% Tween 20 was mixed with 15 µl of RTS reaction (to a final concentration of 0.05 wt % Tween 20), and 15-µl volumes were transferred to 384-well plates. The plates were centrifuged at 1,600×g to pellet any precipitate, and supernatant was printed without further purification onto nitrocellulose-coated FAST glass slides (Schleicher & Schuell; in general, microporous nitrocellulose coated onto glass at a thickness of about 12-14 micron, sufficiently flat to allow laminar flow, and enclosed in a reaction volume of less than 20 microliter) by using an OmniGrid 100 microarray printer (Genomic Solutions, Ann Arbor, Mich.). All ORFs were spotted in duplicate to enable statistical analysis of the data. Data values reported herein represent the average of pairs. In addition, each chip contained an area printed with controls consisting of RTS reaction using no DNA.

A typical device can be constructed according to the following 4-step protocol: (1) A pre-spotted protein array nitrocellulose pad is coupled to a glass slide and the pad is masked using a substrate that is minimally affected by plasma oxidation (e.g., glass, PDMS, polycarbonate). (2) The pre-spotted protein array nitrocellulose pad is then placed in a plasma cleaner to activate the glass surface of the slide and the PDMS of a prefabricated microfluidics system (that provides the fluid channels, reservoirs, cavity layer, and remaining portion of the reaction volume) for irreversible binding. The two portions are placed into the plasma chamber for a set amount of time (typically 1.5 min) before binding takes place. (3) Upon removal of the pre-spotted protein pad, the substrate used to mask the proteins is removed and the PDMS microsystem is aligned and placed in contact with the nitrocellulose coated glass substrate. The contact between the glass and PDMS forms an irreversible seal after a plasma treatment has taken place. However, if an extended period of time occurs after plasma treatment and PDMS-glass contact is made then irreversible binding will not take place. (4) If irreversible binding can not be immediately done after removal from the plasma cleaner, both parts can be placed in an inert gas, for example, for an extended binding window. Binding the two substrates will allow for an irreversible bound between the PDMS and glass even after long periods of time after plasma treatment. Through irreversible binding the PDMS microsystem to the glass substrate, it allows for an environmentally protected protein array within the system.

Figure 3:
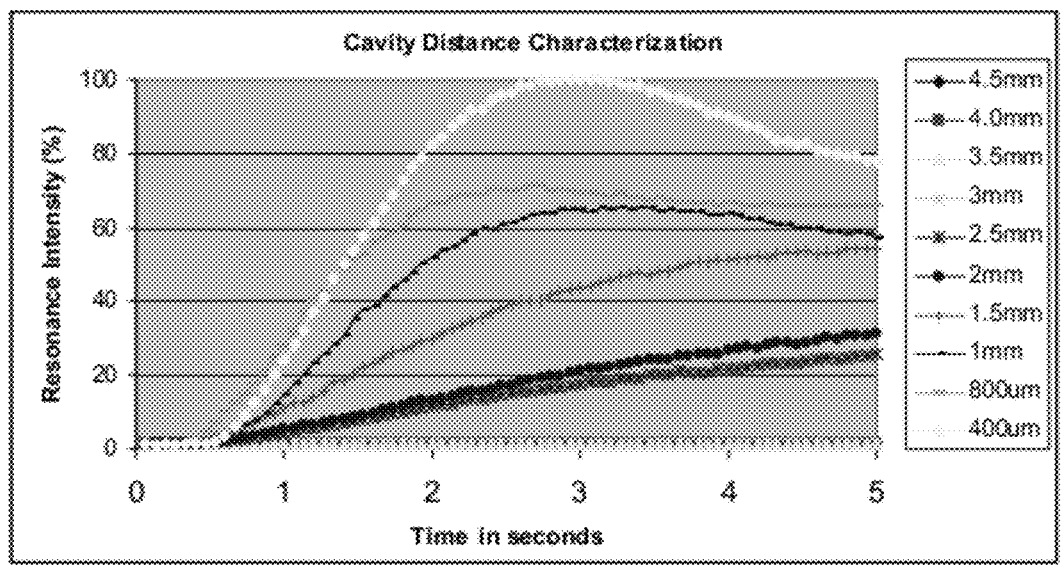
FIG. 3 is a graph depicting resonance intensity for varying bubble cavity distances for an 800 micron bubble over a time scale of 5 seconds for a 400 micrometer distance.
Figure 4:
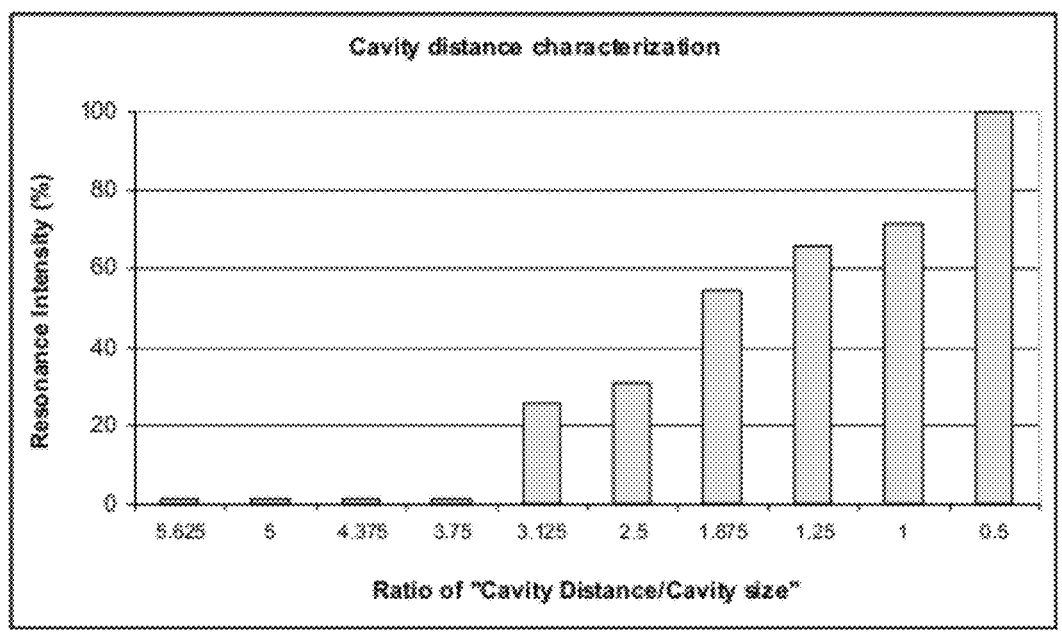
FIG. 4 is a graph depicting maximum resonance intensities for varying ratios of bubble cavity distances to cavity size.

Bubble mixing parameters: Characterization of bubble cavity distances and its effect on resonance was done on a polycarbonate substrate. Cavities approximately 800 microns in diameter were machine drilled at 400 microns deep in a 4 by 4 array, a total of 16 cavities. Results suggest that shorter cavity to cavity distances for the bubbles produce higher resonance intensities. This can be seen in FIG. 3, showing a plot of resonance intensity for varying bubble cavity distances for an 800 micron bubble over a time scale of 5 seconds for the 400 micrometer distance. Similarly, FIG. 4 depicts a plot of maximum resonance intensities for varying ratios of bubble cavity distances to cavity size of an 800 micron diameter bubble in which the ratio of 0.5, or 400 micrometer distance divided by 800 micron diameter, has the highest resonance. This ratio of cavity distance to cavity diameter was then applied as the optimum array format for the colorimetric microfluidic device. Using 100 diameter micron holes at 50 microns deep, each bubble cavity distanced 50 microns apart over a 6000 by 6000 micron surface area, a total of 1600 bubble cavities.

Figure 5:
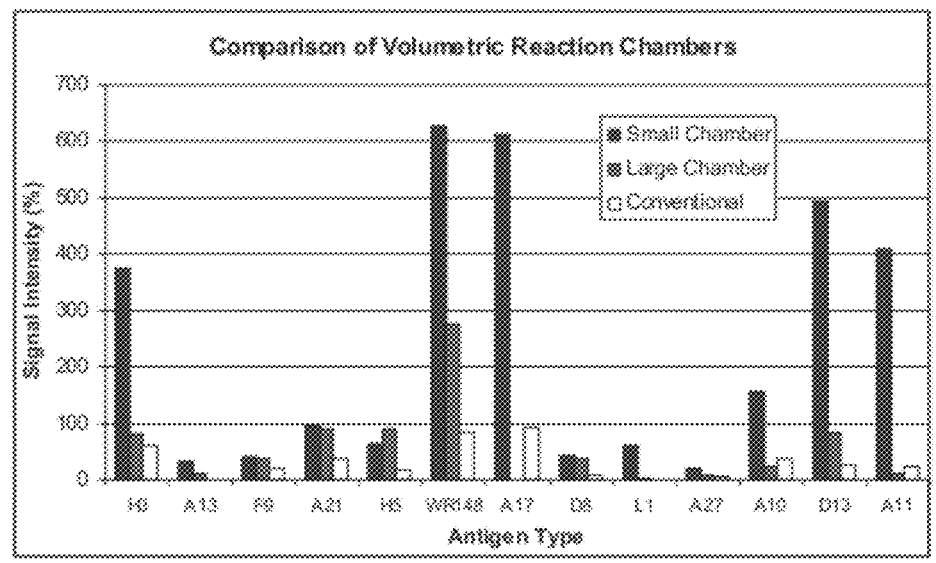
FIG. 5 is a graph depicting performance comparison of volumetric reaction chambers against conventional fluid handling methods.

Comparison of volumetric reaction chambers: Two types of reaction chambers were developed for the PDMS microfluidic device. The small chamber was approximately 3.6 microliters (typically between 3-4 microliters) in volume while the large chamber was approximately 18 microliters in volume. Both utilized an acoustic bubble micromixer that incorporates a 1600 bubble array of 100 micron sized bubbles spaced 50 microns edge to edge. An administered volume of 7 nanoliters of presentable primary antibody immuno-globulin was introduced within the smaller chamber, 9 nanoliters within the larger chamber, and 10 nanoliters for the conventional pipetting approach each for total time of 10 minutes. Results show higher signal intensities for the smaller chamber that utilized microfluidic-flow methods in addition to mixing whereas the large chamber utilized stagnant mixing. The conventional pipetting method relied primarily on diffusion only to produce binding, and shows lower signal intensity in comparison to both microfluidic approaches. Typical results are illustrated in FIG. 5 showing a performance comparison of volumetric reaction chambers against conventional pipetting methods using analogous experimental protocols.

Figure 6:
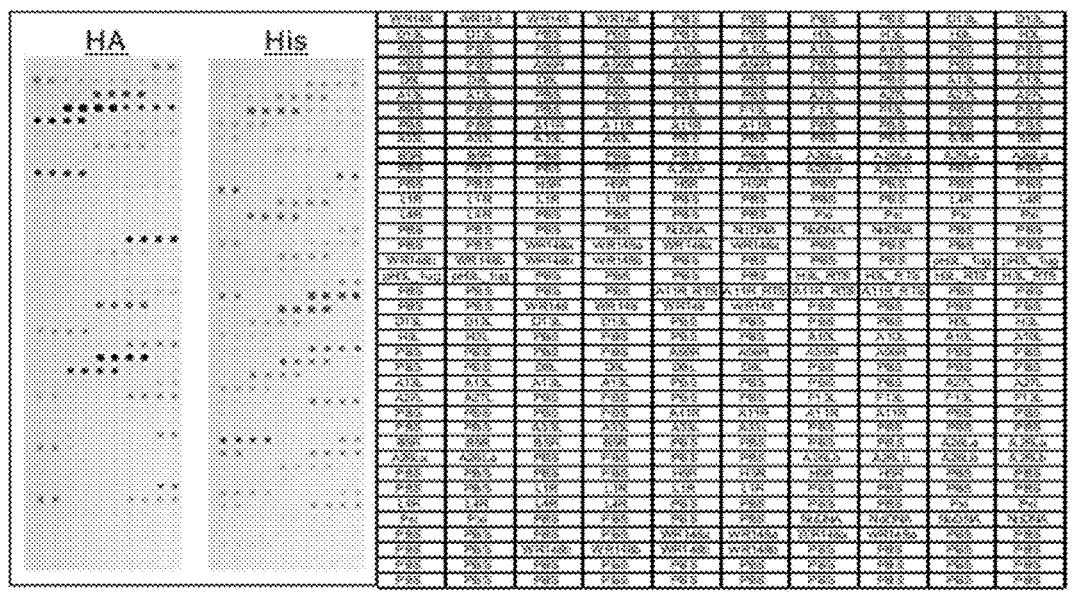
FIG. 6 is an exemplary scan of a protein array (Vaccinia, unpurified) probed with anti-His and Anti-HA antibodies for which corresponding peptides are denoted in the adjacent table.
Figure 7:
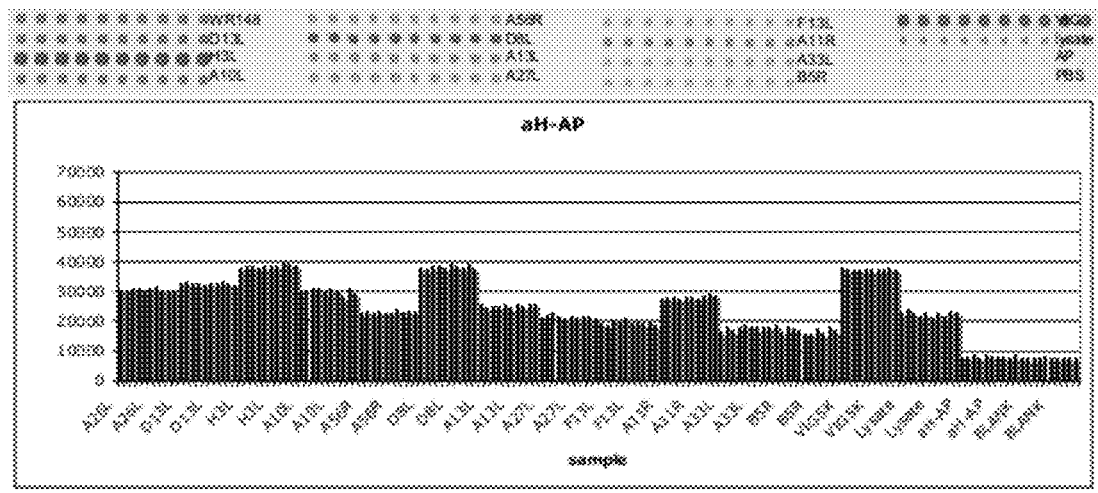
FIG. 7 is another exemplary scan of a protein array (Vaccinia, unpurified) in which binding of human immunoglobulin was quantified using ProScanArray, and in which the highly reproducible corresponding signal intensities are depicted in the graph below.

An enzyme based detection system was used that produced a precipitate on a white background. Results of exemplary tests are depicted in FIG. 6 in which a Vaccinia unpurified protein chip was probed with anti-His and Anti-HA antibodies. FIG. 7 illustrates another Vaccinia unpurified protein chip probed with Vaccinia Immunoglobulin, which was quantified using ProScanArray after manipulating the scanned image. As can be clearly seen, results are highly reproducible in a quantitative fashion.

Comparative Time Requirements And Sensitivity for Microfluidic and Conventional Analysis: The order of reagents required to identify targeted biomarkers is: (1) blocking buffer, (2) serum sample or primary reagent containing primary antibodies, (3) washing, (4) secondary reagent, (5), washing, (6) substrate reagent, and (7) washing. Reagents were received a day prior to experimentation. Serum sample was composed of *E. coli* lysate, blocking buffer, and approximately 0.05% of primary antibody vaccinia-immuno-globulin (VIG, for arrays where vaccinia proteome was spotted). Secondary reagent comprised of 0.5% anti-human IgA IgG IgM (H+L) alkaline phosphatase-conjugated Affini Pure Goat diluted in blocking buffer. Substrate solution comprised of 5-bromo-4-chloro-3 indolyl phosphate (BCIP) p-Toluidine salt, nitroblue tetrazolium (NBT), and AP developing buffer. Of course, it should be appreciated that numerous alternative precipitating dyes are also suitable and include 3-amino-9-ethylcarbazole, 5-bromo-4-chloro-3-indolylphosphate, 3-3'-diaminobenzidine tetrachloride, 3,3',5,5'-tetramethylbenzidine, and even colloidal metals. Further suitable compounds are described in U.S. Pat. No. 6,251,618, which is incorporated by reference herein.

A comparison test was done between conventional testing methods versus the microfluidic approach using analogous procedures, reagents, and fabrication setups as depicted in the tables below. The microfluidic device's 'on-chip' acoustic micromixer was set at a frequency of 3.6 kHz and amplitude of 30 Vpp (Volt peak-to-peak) and 20 Vpp (Volt peak-to-peak) for step 2 and step 4, respectively. Step 2 was performed in a flow and stop method in which flow was administered for 15 seconds then stopped for 30 seconds and restarted in a repetitive cycle totaling 10 minutes and 30 seconds.

| Step | Time (min) | Volume (µL) |
|---|---|---|
| 1 | 5 | 25 |
| 2 | 10 | 20 |
| 3 | 2 | 20 |
| 4 | 10 | 20 |
| 5 | 2 | 20 |
| 6 | 7 | 14 |
| 7 | 1 | 10 |

Conventional approach

| Step | Time (min) | Volume (µL) | Flow Rate (µL/min) |
|---|---|---|---|
| 1 | 5 | 25 | 5 |
| 2 | 10 | 14 | 4 |
| 3 | 2 | 20 | 10 |
| 4 | 10 | 20 | 2 |
| 5 | 2 | 20 | 10 |
| 6 | 7 | 14 | 2 |
| 7 | 1 | 10 | 10 |

Microfluidic appproach

Figure 8:
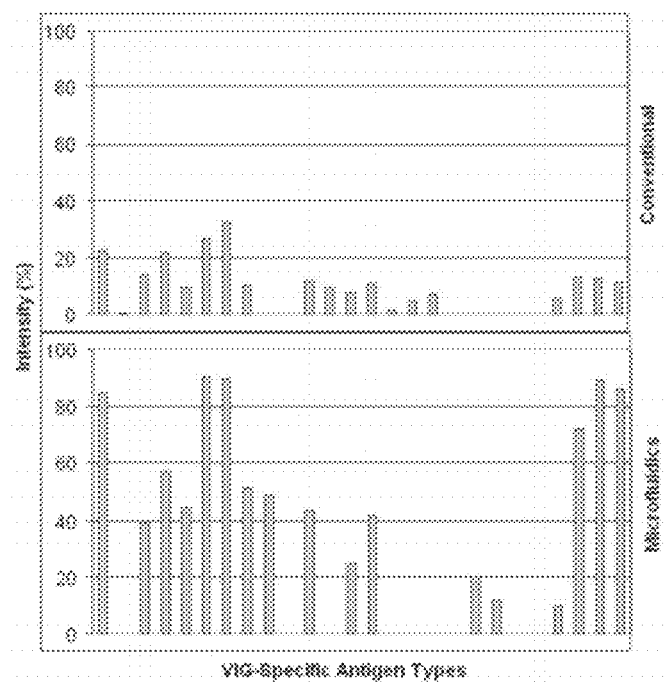
FIG. 8 is a graph depicting a comparison of binding sensitivity between contemplated microfluidic device hybridization and conventional hybridization using VIG antibody.
Figure 9:
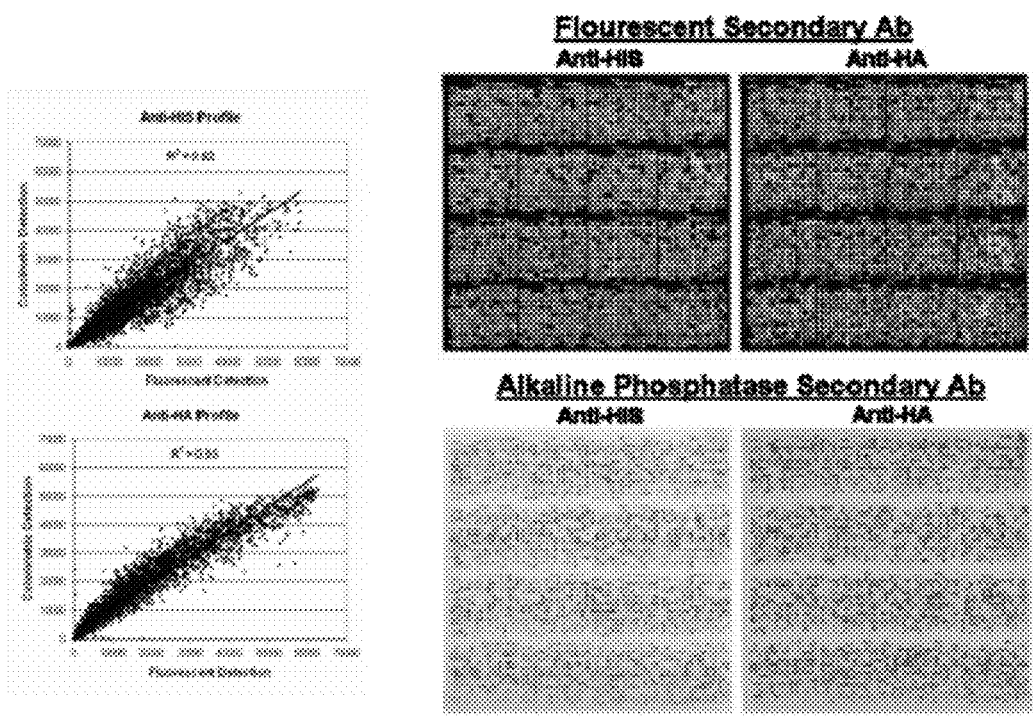
FIG. 9 depicts exemplary scans and corresponding graph illustrating high correlation between test results obtained by fluorescence detection (top) and colorimetric dye detection (bottom) using two distinct secondary antibodies on a total of over 4600 antigens.

Completed tests were scanned and processed using Perkin-Elmer ScanArray Express. Each spot is numerically quantified based on the intensity of the chromogenic reaction product signifying antibody-antigen binding. All target-specific antigen (VIG) intensities were standardized according to 'No DNA' controls and any false positives within non-targeted antigens. The final calculation gave a standardized percentage difference in signal intensity that is plotted in a chart. Results in FIG. 8 show a higher binding sensitivity through the microfluidic approach needing only 7 nanoliters VIG antibody. Although 10 nanoliters VIG antibody is used for the conventional method, detection sensitivity and binding intensity is much lower. Results for the following microfluidic design suggests a potential detection system for reducing reagent volumes and testing times while still maintaining high levels of sensitivity unachievable through conventional lab-bench processes. FIG. 9 exemplarily depicts the high correlation between test results obtained by fluorescence detection and colorimetric dye detection using over 4600 antigens.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A microfluidic device, comprising:
    an enclosed reaction volume between 1 µl and 50 µl, formed at least in part by a non-permeable glass or transparent polymer carrier material, and wherein the reaction volume is configured to allow retention of a solution comprising an antibody;
    a porous optical contrast layer having a thickness of between 10-100 microns and coupled to a surface of the glass or transparent polymer carrier material, wherein the optical contrast layer is disposed within the reaction volume and opposite to a cavity layer within the reaction volume, and wherein the cavities in the cavity layer are circular cavities arranged at regular intervals in x- and y-coordinate;
    wherein a plurality of distinct antigens are non-covalently and non-specifically bound to the optical contrast layer as antigen spots in respective predetermined positions, and wherein the optical contrast layer comprises a nontransparent material;
    wherein the cavity layer is configured to provide a plurality of cavities having a radius of 400 µm or less and configured to allow trapping of air in the plurality of cavities, and wherein the plurality of cavities are (a) sized and positioned to allow acoustic air bubble resonance mixing of a fluid that is in contact with the optical contrast layer and provide a cavity distance/cavity size ratio of 3.125 or less, and (b) positioned opposite to the plurality of distinct antigens;
    wherein the number and/or size of the cavities is selected to allow substantially complete hybridization of the antibody to at least one of the plurality of antigens within less than 60 minutes upon contacting the antigens with the antibody when oscillated at a frequency of 3.6 kHz; and
    wherein a ratio between a number of the antigen spots to a number of cavities is at least 3:1, and wherein a ratio between an area of an antigen spot and cavity diameter is at least 1:3.

2. The microfluidic device of claim 1 wherein the plurality of distinct antigens are bound to the optical contrast layer as a crude expression reaction.

3. The microfluidic device of claim 2 wherein the crude expression reaction further comprises a detergent.

4. The microfluidic device of claim 1 wherein the antigen spots comprise a dye selected from the group consisting of 3-amino-9-ethylcarbazole, 5-bromo-4-chloro-3-indolylphosphate, 3-3'-diaminobenzidine tetrachloride, 3,3',5,5'-tetramethylbenzidine, and a colloidal metal.

5. The microfluidic device of claim 1 wherein the carrier material and the optical contrast layer are configured to allow optical detection from opposite sides of the optical contrast layer.

6. The microfluidic device of claim 1 wherein at least two of the distinct antigens have known quantified and known relative reactivities with respect to sera of a population infected with a pathogen expressing the antigens.

7. The microfluidic device of claim 6 wherein the at least two of the distinct antigens are from the same pathogen.

8. The microfluidic device of claim 1, wherein a transparent topmost layer comprises the cavity layer, the device further comprising an imaging detector including a lens and configured to detect a secondary reagent bound to the antibody and the antibody hybridized to one of the plurality of distinct antigens bound to the optical contrast layer through the topmost transparent layer, wherein the optical contrast layer comprises nitrocellulose and is positioned at a bottom of the chamber.

9. The microfluidic device of claim 1, wherein cavities of the plurality of cavities have a diameter of about 100 µm.

10. The microfluidic device of claim 1, wherein the plurality of cavities comprises more than 1,000 cavities.

11. The microfluidic device of claim 1, wherein the porous optical contrast layer comprises a porous membrane, and wherein the porous membrane comprises a plurality of pores having sizes ranging from 0.2 µm and 0.5 µm.

* * * * *